(12) United States Patent
Joshi et al.

(10) Patent No.: US 7,790,916 B2
(45) Date of Patent: Sep. 7, 2010

(54) CARBOCYCLIC AND OXACARBOCYCLIC FUMARIC ACID OLIGOMERS

(75) Inventors: Rajendra Kumar Joshi, Zürich (CH); Hans-Peter Strebel, Lucerne (CH)

(73) Assignee: Biogen Idec International GmbH, Zug (CH)

( * ) Notice: Subject to any disclaimer, the term of this patent is extended or adjusted under 35 U.S.C. 154(b) by 490 days.

(21) Appl. No.: 10/511,564

(22) PCT Filed: Apr. 3, 2003

(86) PCT No.: PCT/EP03/03498

§ 371 (c)(1), (2), (4) Date: Oct. 15, 2004

(87) PCT Pub. No.: WO03/087174

PCT Pub. Date: Oct. 23, 2003

(65) Prior Publication Data

US 2005/0148664 A1    Jul. 7, 2005

(30) Foreign Application Priority Data

Apr. 18, 2002 (DE) ................. 102 17 314

(51) Int. Cl.
- *C07C 69/74* (2006.01)
- *C07C 69/75* (2006.01)
- *C07D 321/12* (2006.01)
- *A61K 31/215* (2006.01)
- *A61K 31/194* (2006.01)
- *A61K 31/357* (2006.01)

(52) U.S. Cl. ................. 560/127; 560/123; 562/505; 562/509

(58) Field of Classification Search ................. None
See application file for complete search history.

(56) References Cited

U.S. PATENT DOCUMENTS

| | | | |
|---|---|---|---|
| 3,139,395 A | | 6/1964 | Griffin |
| 3,253,016 A | | 5/1966 | Griffin |
| 3,920,837 A | * | 11/1975 | Schmidt-Dunker et al. ... 514/574 |
| 4,086,334 A | | 4/1978 | Schmidt-Dunker et al. |
| 4,851,439 A | | 7/1989 | Speiser et al. |
| 4,959,389 A | | 9/1990 | Speiser et al. |
| 5,042,986 A | * | 8/1991 | Kitchens et al. ................. 8/120 |
| 5,424,332 A | | 6/1995 | Speiser et al. |
| 5,451,667 A | | 9/1995 | Speiser et al. |
| 5,631,401 A | * | 5/1997 | Stein et al. ................. 562/451 |
| 6,277,882 B1 | | 8/2001 | Joshi et al. |
| 6,355,676 B1 | | 3/2002 | Joshi et al. |
| 6,359,003 B1 | | 3/2002 | Joshi et al. |
| 6,436,992 B1 | | 8/2002 | Joshi et al. |
| 6,509,376 B1 | | 1/2003 | Joshi et al. |
| 6,858,750 B2 | | 2/2005 | Joshi et al. |
| 2004/0038889 A1 | | 2/2004 | Joshi et al. |
| 2004/0054001 A1 | | 3/2004 | Joshi et al. |

FOREIGN PATENT DOCUMENTS

| | | |
|---|---|---|
| DE | 2212369 A | 9/1973 |
| DE | 2417788 | 10/1975 |
| DE | 2530372 | 1/1977 |
| DE | 2543351 | 4/1977 |
| DE | 2621214 | 11/1977 |
| DE | 3834794 | 4/1990 |
| DE | 19721099 A1 | 11/1998 |
| DE | 19839566 A1 | 3/2000 |
| DE | 19853487 A1 | 5/2000 |
| DE | 10000577 A1 | 7/2001 |
| DE | 10101307 A1 | 8/2002 |
| EP | 0188749 A2 | 7/1986 |
| EP | 0312697 A2 | 4/1989 |
| FR | 1563486 A | 4/1969 |
| GB | 1216699 | 12/1970 |
| GB | 1422726 | 1/1976 |
| WO | WO 89/01930 | 3/1989 |
| WO | WO 94/28883 | 12/1994 |
| WO | WO 95/12572 | 5/1995 |
| WO | WO 95/12572 A1 | 5/1995 |
| WO | WO 95/21815 | 8/1995 |
| WO | WO 98/52549 A2 | 11/1998 |
| WO | WO 99/21565 | 5/1999 |
| WO | WO 99/49858 A1 | 10/1999 |
| WO | WO 00/12072 A2 | 3/2000 |
| WO | WO 00/23068 A2 | 4/2000 |
| WO | WO 00/30622 A2 | 6/2000 |
| WO | WO 01/51047 A1 | 7/2001 |
| WO | WO 02/055063 A2 | 7/2002 |
| WO | WO 02/055066 A1 | 7/2002 |

OTHER PUBLICATIONS

Doerhoefer et al. Tel. Let. 1966, 37, 4511-4516; see abstract and structure in the attached CAPLUS printout.*

(Continued)

*Primary Examiner*—Daniel M Sullivan
*Assistant Examiner*—Yevegeny Valenrod
(74) *Attorney, Agent, or Firm*—Finnegan, Henderson, Farabow, Garrett & Dunner, LLP

(57) ABSTRACT

The present invention relates to certain carbocyclic and oxacarbocyclic fumaric acid oligomers and the use thereof for preparing a pharmaceutical preparation as well of pharmaceutical preparations containing these compounds.

17 Claims, No Drawings

OTHER PUBLICATIONS

Griffin et al. Journal of the American chemical society 1962, vol. 84 p. 1012-15.*

Vellturo et al. Journal of Organic Chemistry, 1966, 31(7), 2241-2244.*

Altmeyer, P., Dr., et al., "Systemische Therapie der Psoriasis", T & E Dermatologie Jg., 27, 1997, pp. 380-384. Not translated.

Bayard, W., et al., "Perorale Langzeitbehandlung der Psortiasis mit Fumarsaurederivaten" Hautarzt, May 1987, 38(5), pp. 279-285. Not translated.

Medline Abstract of Bayard, W., et al., "[Peroral long-term treatment of psoriasis using fumaric acid derivatives]", Hautarzt, May 1987, 38(5), 1 page.

Farina, Mario, et al., "Stereochemical Study of 1,2,3,4,5,6-Hexakis(methoxycarbonyl)cyclohexanes", J. Am. Chem. Soc., 1985, vol. 107, pp. 5100-5104.

Griffin, G.W., et al., "The Chemistry of Photodimers of Maleic and Fumaric Acid Derivatives. 1. Dimethyl Fumarate Dimer", Dimethyl Fumarate Dimer, vol. 83, Jun. 20, 1961, pp. 2725-2728.

Hunziker. Th., et al., "Is Psoriasis an Autoimmune Disease?", excerpt from Therapeutische Umschau, Dermatological Clinic of the University of Berne, vol. 50, 1993, $2^{nd}$ edition, 5 pages.

Maier, Martin E., "Synthesis of Medium-Sized Rings by the Ring-Closing Metathesis Reaction", Angew. Chem. Int. Ed. 2000, vol. 39, No. 12, pp. 2073-207.

Sebok, B., et al., "Effect of Fumaric Acid, Its Dimethylester, and Topical Antipsoriatic Drugs on Epidermal Differentiation in the Mouse Tail Model", Skin Pharmacol, 1996, vol. 9, pp. 99-103.

International Search Report completed Oct. 31, 2003 for PCT/EP2003/03498.

International Preliminary Examination Report completed Feb. 12, 2004 for PCT/EP2003/03498.

Non-final Office Action mailed Nov. 14, 2008, in U.S. Appl. No. 11/833,150, filed Aug. 2, 2007.

Final Office Action mailed Feb. 12, 2007, in U.S. Appl. No. 10/250,983, filed Jul. 10, 2003.

Non-final Office Action mailed Jul. 20, 2006, in U.S. Appl. No. 10/250,983, filed Jul. 10, 2003.

* cited by examiner

CARBOCYCLIC AND OXACARBOCYCLIC FUMARIC ACID OLIGOMERS

REFERENCE TO RELATED APPLICATIONS

This application is a 371 continuation of PCT Application PCT/EP03/03498 filed Apr. 3, 2003, the text of which is not in English, which PCT Application claims priority on German Application No. 102 17 314.1, filed Apr. 18, 2002 the text of which is not in English.

The present invention relates to certain carbocyclic and oxacarbocyclic fumaric acid oligomers, to the use thereof for preparing a pharmaceutical preparation and to pharmaceutical preparations containing said compounds.

For a long time, fumaric acid dialkyl esters as well as fumaric acid monoalkyl esters and salts thereof have been successfully used for treating psoriasis. Said use is described in a number of patents, for example DE-25 30 372, DE 26 21 214 or EP-B-0 312 697.

The use of fumaric acid mono- and diesters is also described for the treatment of autoimmune diseases such as polyarthritis or multiple sclerosis (cf. DE 197 21 099.6 and DE 198 53 487.6), but also for use in transplantation medicine (cf. DE 198 53 487.6 and DE 198 39 566.3). The use of fumaric acid mono- and diesters for the treatment of NF-kappaB mediated diseases and the treatment of mitochondrial diseases is also known from DE 101 01 307.8 and DE 100 00 577.2. However, all the cited documents merely describe fumaric acid mono- and diesters, optionally in the form of certain salts.

Because of their volatility and sublimability, however, the above-mentioned fumaric acid esters have the disadvantage of being difficult to handle when preparing pharmaceutical products, especially those in solid form for oral administration. Specifically the preparation of such products requires protective measures such as the use of breathing masks, gloves, protective clothing, etc.

In addition, the fumaric acid esters are absorbed in the gastro-intestinal tract after oral administration and taken up unspecifically from the bloodstream by ail body cells. Therefore, it is necessary to administer high dosages. Such high dosages in turn lead to the known side effects of a fumaric acid therapy like flush symptoms (reddening) or gastrointestinal irritation (nausea, diarrhea, winds). Even though such side effects may be reduced considerably by administering the active ingredient in the form of micro-tablets as described in the above-cited prior art, they cannot be avoided altogether.

At the same time, the fumaric acid esters are rapidly hydrolysed in the blood and the products of said hydrolysis, alcohol and fumaric acid or fumaric acid monoester, metabolised. In order to maintain therapeutically effective levels repeated and frequent administration is therefore necessary. Even though a certain adaptation is observed concerning the side effects, a further reduction of the side effect rate would be desirable.

In order to avoid these disadvantages fumaric acid mono- and -diamides are known from non-prepublished DE 101 33 004.9. These amides are formed with amino acids and preferably with certain peptides. Bonding to a peptide has the objective of specific delivery of the fumaric acid derivative to individual target cells. However, the respective fumaric acid-peptide derivatives have the disadvantage of being expensive to produce.

Therefore, it is an object of the present invention to provide fumaric acid derivatives, which are more resistant to hydrolysis and easier to produce and to handle, and to provide the use of such derivatives.

This object is achieved by certain carbocyclic and oxacarbocyclic fumaric acid oligomers, the use thereof for preparing pharmaceutical preparations and pharmaceutical preparations containing these oligomers.

More specifically, the present invention, in a first aspect, relates to carbocyclic and oxacarbocyclic fumaric acid oligomers containing 2 to 10 units derived from fumaric acid and/or esters and/or amides as repeating units. These carbocyclic and oxacarbocyclic fumaric acid oligomers are preferably obtained by olefinic polymerization of C—C double bonds or polarised olefinic polymerisation of the C—C double bonds and carbonyl oxygens of the units, respectively. Preferably, these units derived from fumaric acid are derived from monomers selected from the group consisting of fumaric acid, dialkyl fumarates, monoalkyl hydrogen fumarates, fumaric acid monoamides, fumaric acid diamides, monoalkyl monoamido fumarates, and salts and mixtures thereof. More preferably, the oligomer of the invention contains units derived from only one or two monomers; most preferably, the oligomer exclusively contains identical monomer units. Preferably the monomers are not the fumaric acid itself but one of the above-mentioned derivatives, especially the mono- or dialkyl fumarates.

The carbocyclic oligomer of the invention is composed or consists of the units derived from the fumaric acid in such a way that the units are linked by covalent C—C bonds at the C atoms 2 and 3 of the fumaric acid skeleton so that a carbocyclic oligomer is produced. The C—C bonds may be generated by olefinic polymerisation of the double bonds. The carbocyclic fumaric acid oligomer of the invention preferably does not contain any olefinic unsaturations in the backbone.

In the carbocyclic oligomers of the invention, the oligomer backbone (the carbocycle) consists of fumaric acid units, i.e. it has a even number of C atoms and does not contain any other monomers and/or hetero atoms. At each C atom this backbone is substituted by one of the carboxylic acid or carboxylic acid amide groups of the fumaric acid monomer unit(s) of which it is composed. During synthesis, the monomer units may be present through polymerisation of the derivatives in the form of the esters or amides, but also in the form of salts.

The oxacarbocyclic oligomer of the invention is composed of the fumaric acid-monomers in such a manner that the units are linked by ether bridges at the C atoms 1 and 3. At the same time, the ethylenic unsaturation shifts from the atoms $C_2$ and $C_3$ to $C_1$ and $C_2$. In the case of the oxacarbocyclic oligomers of the invention, the ring therefore contains polyoxypropene units.

The term "oligomer" used herein refers to a number of at least two fumaric acid monomer units. The carbocyclic fumaric acid oligomer usually contains 2 to 10, preferably 2 to 6 and most preferably 2 to 3 units derived from fumaric acid. In general, these may polymerise with each other or be linked for formation of the carbocycle in any steric arrangement. Preferably, all of the carboxylic acid or carboxylic acid amide groups as substituents of the fumaric acid units in the oligomer of the invention are in a trans position to each other, i.e. to each of the adjacent carboxylic acid or carboxylic-acid amide groups.

In a preferred embodiment, the invention relates to a carbocyclic fumaric acid oligomer represented by the following formula (I)

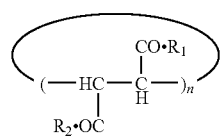

wherein the residues $R_1$ and $R_2$ are the same or different and are selected from the group consisting of amine-residues ($-NR_3R_4$), amino acid residues ($-NH-C(COOH)-R_6$), peptide residues having 2 to 100 amino acids, alcohol residues ($-OR_5$) and a hydroxyl residue, n is an integer from 2 to 10 inclusive, the residues $R_3$ and $R_4$ are the same or different and are selected from the group consisting of hydrogen, $C_{1-24}$ alkyl residues, the phenyl residue and $C_{6-10}$ aralkyl residues, the residue $R_5$ is selected from the group consisting of hydrogen, $C_{1-24}$-alkyl residues, the phenyl residue and $C_{6-10}$ aralkyl residues, and the residue $R_6$ represents a side chain of a natural or synthetic amino acid.

In a first embodiment, it is preferred that each of the residues $R_1$ and $R_2$ independently represent an alcohol or hydroxyl residue. Preferably, $R_1$ and $R_2$ are not both hydroxyl. Therefore, the monomer(s) preferably is/are one or several monoalkyl hydrogen fumarate(s). In another embodiment, both residues $R_1$ and $R_2$ may represent an alkoxy residue $-OR_5$ which, even more preferably, is identical. In this case, the monomer(s) is/are dialkyl fumarate(s).

Preferably, $R_1$ and $R_2$ are independently selected from the group consisting of hydroxyl, methoxy, ethoxy, propoxy, isopropoxy, n-butoxy, sec-butoxy, tert-butoxy, phenoxy and pentoxy, most preferably methoxy and/or ethoxy. Accordingly, carbocyclic oligomers, derived from dimethyl fumarate, diethyl fumarate, methyl ethyl fumarate, methyl hydrogen fumarate and ethyl hydrogen fumarate are especially preferred. Most preferred is a carbocyclic fumaric acid oligomer of the formula (I) wherein $R_1$ and $R_2$ both identically represent methoxy or ethoxy.

It goes without saying that monomers bearing a carboxy function and the corresponding polymers of the invention (wherein $R_1$ and/or $R_2 = -OH$ or $-O^-$) may be present in the form of their salts. The alkali metal salts such as Li, Na, K, the alkaline earth metal salts such as Mg, Ca, and the salts of physiologically acceptable transition metals, especially Fe and Zn, are preferred.

According to a third preferred embodiment, the invention relates to a carbocyclic oligomer, especially of the above formula (I), wherein $R_1$ is an amine residue $-NR_3R_4$ or an amino acid-residue $-NH-C(COOH)-R_6$ bound via an amide link and $R_2$ is an amine residue $-NR_3R_4$, an alcohol residue $-OR_5$ or $-OH$.

As defined above, the residue $R_6$ may be a side chain of any natural or synthetic amino acid. The amino acid residue may be present in L or D configuration, the L configuration being preferred. Preferably, $R_6$ is selected from the group consisting of the side chains of Ala, Val, Leu, Ile, Pro, Trp, Phe, Met, Gly, Ser, Tyr, Thr, Cys, Asn, Gln, Asp, Glu, Lys, His, Arg, Orn, Hcy, Hse, Hyp, and Sar.

Preferably, the residues $R_3$, $R_4$ and $R_5$ are the same or different and are selected from the group consisting of hydrogen, methyl, ethyl, n-propyl, isopropyl, n-butyl, sec-butyl, t-butyl, pentyl, cyclopentyl, 2-ethyl hexyl, hexyl, cyclohexyl, heptyl, cycloheptyl, octyl, vinyl, allyl, 2-hydroxyethyl, 2- or 3-hydroxypropyl, 2,3-dihydroxypropyl, 2-methoxyethyl, methoxymethyl and 2- or 3-methoxypropyl.

In an especially preferred embodiment, the invention relates to a carbocyclic fumaric acid oligomer represented by the formula (II)

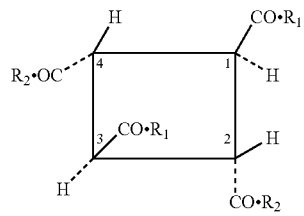

which may be called r-1,t-2,c-3,t-4-tetrakis(alkoxycarbonyl)cyclobutane or r-1,t-2,c-3,t-4-cyclobutane tetracarboxylic acid alkyl ester, or represented by the formula (III)

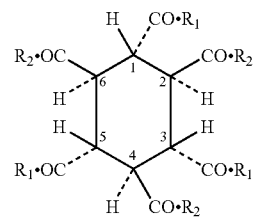

which may be called r-1,t-2,c-3,t-4,c-5,t-6-hexa(alkoxycarbonyl)cyclohexane or r-1,t-2, c-3,t-4,c-5,t-6-cyclohexane hexacarboxylic acid alkyl ester.

Most preferably, the invention relates to a carboxylic fumaric acid oligomer represented by the formula (IIa)

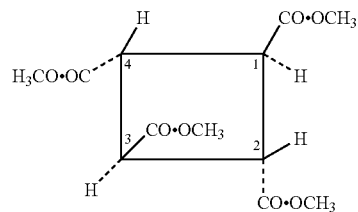

which may be called r-1,t-2,c-3,t-4-tetrakis(methoxycarbonyl)cyclobutane or r-1,t-2,c-3,t-4-cyclobutane tetracarboxylic acid methyl ester or of the formula (IIIa)

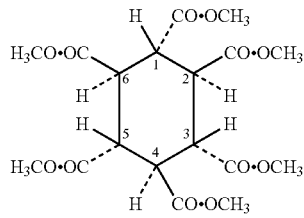

which may be called r-1,t-2,c-3-t-4,c-5,t-6-hexa(methoxycarbonyl)cyclohexane or r-1,t-2,c-3,t-4,c-5,t-6-cyclohexane hexacarboxylic acid methyl ester.

In another preferred embodiment, the invention relates to an oxacarbocyclic fumaric acid oligomer represented by the following formula (IV)

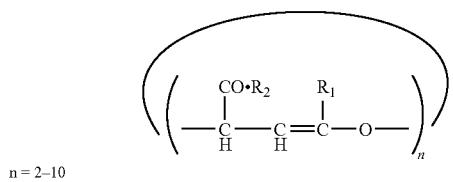

n = 2–10 wherein the residues $R_1$ and $R_2$ are the same or different and are selected from the amine residues (—$NR_3R_4$), amino acid residues (—NH—C(COOH)—$R_6$), peptide residues having 2 to 100 amino acids, alcohol residues (—$OR_5$) and a hydroxyl residue, n is an integer from 2 to 10 inclusive, the residues $R_3$ and $R_4$ are the same or different and are selected from the group consisting of hydrogen, $C_{1-24}$ alkyl residues, the phenyl residue and $C_{6-10}$ aralkyl residues, the residue $R_5$ is selected from the group consisting of hydrogen, $C_{1-24}$ alkyl residues, the phenyl residue and $C_{6-10}$ aralkyl residues, and the residue $R_6$ represents a side chain of a natural or synthetic amino acid.

Preferably, $R_1$, $R_2$, $R_3$, $R_4$, $R_5$, and $R_6$ are as defined above. More preferably, $R_1$ and $R_2$ are alkoxy residues —$OR_5$ or hydroxy, and, most preferably, $R_1$ and $R_2$ are methoxy or ethoxy ($R_1$ and $R_2$ are alkoxy and $R_5$ is methyl or ethyl). The index n preferably is 2 or 3.

According to an especially preferred embodiment, the oxacarbocyclic fumaric acid oligomer is preferably represented by the formula (V)

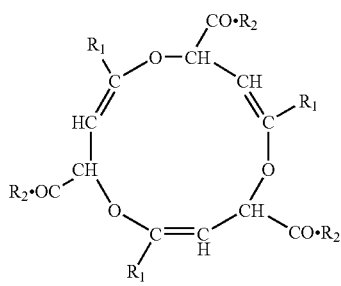

wherein $R_1$ and $R_2$ are defined as above, or the formula (VI)

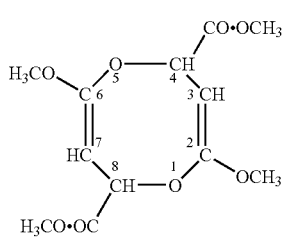

The compound of the formula (VI) may be called dimethyl-2,6-dimethoxy-1,5-dioxacyclo-2,6-octadiene-4,8-dicarboxylate or dimethyl-2,6-dimethoxy-1,5-dioxacycloocta-2,6-diene-4,8-dicarboxylate.

The carbocyclic and oxacarbocyclic fumaric acid oligomers of the invention may be prepared by well known processes for preparing cyclic compounds. For example, they may be prepared with the aid of known cyclisation agents such as boron compounds, polyphosphoric acids etc. under the usual conditions.

The carbocyclic fumaric acid oligomers of the invention are preferably prepared by a photopolymerisation process. As is customary in such processes, polymerisation is induced by irradiation of the monomers, usually in the liquid phase and, optionally, in combination with a suitable conventional solvent inert to polymerisation, such as an alkane, cycloalkane or aromatic solvent, with light of a wavelength of 200 to 700 nm. If desired, conventional polymerisation initiators such as hydroperoxides, organic peroxides, benzoin methyl ether, benzyl or diacetyl, etc., and/or sensitisers may be added, for example, in order to increase the yield of the reaction. Wavelengths in the UV or blue light range are preferably used for activating the ethylenic unsaturations of the fumaric acid monomer units or other suitable monomer units.

Another preferred process of preparation is the so-called metathesis which, today, is the process practised most frequently for selective polymerisations or ring-closure syntheses. The reactions called metathesis reactions generally are cyclisations or polymerisations catalysed by heavy metal. A general overview is given in the article "Die Olefinmetathese—neue Katalysatoren vergrößern das Anwendungspotential" (Olefin metathesis—new catalysts increase the application potential) by M. Schuster and S. Blechert, "Chemie in unserer Zeit", No. 1, 2001.

Metathesis reactions for preparing the fumaric acid oligomers of the invention may be carried out as homogenous or heterogeneous reactions under the usual conditions and using conventional catalysts. Exemplary catalysts that may be mentioned are those on the basis of Pd, Mo and Ru, especially Grubb's catalyst and Schrock's catalyst. The metatheses may be carried out in conventional solvents such as hydrocarbons (optionally halogenated), especially alkanes, cycloalkanes, aromatic solvents, but also ethers, esters, DMSO, etc. In general, reaction temperatures are below room temperature, for example between –20 and 10° C.

The carbocyclic fumaric acid oligomers of the invention may also be prepared by combining the above-mentioned processes, for example starting with photopolymerisation in order to obtain cyclic and/or linear polymers, followed by ring-closure metathesis, possibly in the form of cleaving the cyclisised molecule (cf. J. Pernerstorfer, M. Schuster and S. Blechert in "Cyclisation/cleavage of macrocycles by ring closing metathesis on solid support-confirmational studies", Chem. Commun. 1997, 1949).

In a second aspect, the invention relates to the use of a carbocyclic fumaric acid oligomer as defined above for preparing a pharmaceutical preparation. In a third aspect, the present invention also relates to a pharmaceutical preparation containing a fumaric acid oligomer as defined above.

The pharmaceutical preparation is preferably intended for treating an autoimmune disease, for use in transplantation medicine and for treating mitochondrial diseases and diseases which may be influenced by NFkappaB. In particular, the pharmaceutical preparation is suitable and destined for (1) for the therapy of an autoimmune disease selected from the group consisting of polyarthritis, multiple sclerosis, graft-versus-host reactions, juvenile-onset diabetes, Hashimoto's thyroiditis, Grave's disease (Basedow disease), systemic Lupus erythematodes (SLE), Sjogren's syndrome, pernicious anaemia and chronic active (=lupoid) hepatitis;
(2) for use in transplantation medicine (host-versus-graft reactions);
(3) for the therapy of mitochondrial diseases selected from the group consisting of Parkinson syndrome, Alzheimer's disease, Chorea Huntington disease, retinopathia pigmentosa or forms of mitochondrial encephalomyopathy; as well as
(4) for the therapy of NF-kappaB mediated diseases selected from the group consisting of progressive systemic sclerodermia, osteochondritis syphilitica (Wegener's disease), cutis marmorata (livedo reticularis), Behcet disease, panarteriitis, colitis ulcerosa, vasculitis, osteoarthritis, gout, arteriosclerosis, Reiter's disease, pulmonary granulomatosis, types of encephalitis, endotoxic shock (septic-toxic shock), sepsis, pneumonia, encephalomyelitis, anorexia nervosa, hepatitis (acute hepatitis, chronic hepatitis, toxic hepatitis, alcohol-induced hepatitis, viral hepatitis, jaundice, liver insufficiency and cytomegaloviral hepatitis), Rennert T-lymphomatosis, mesangial nephritis, post-angioplastic restenosis, reperfusion syndrome, cytomegaloviral retinopathy, adenoviral diseases such as adenoviral colds, adenoviral pharyngoconjunctival fever and adenoviral ophthalmia, AIDS, Guillain-Barré syndrome, post-herpetic or post-zoster neuralgia, inflammatory demyelinising polyneuropathy, mononeuropathia multiplex, mucoviscidosis, Bechterew's disease, Barett oesophagus, EBV (Epstein-Barr virus) infection, cardiac remodeling, interstitial cystitis, diabetes mellitus type II, radiosensitisation of malignant tumours, multi-resistance of malignant cells to chemotherapeutic agents (multipharmaceutical preparation resistance in chemotherapy), granuloma annulare and cancers such as mamma carcinoma, colon carcinoma, melanoma, primary liver cell carcinoma, adenocarcinoma, kaposi's sarcoma, prostate carcinoma, leukaemia such as acute myeloid leukaemia, multiple myeloma (plasmocytoma), Burkitt lymphoma and Castleman tumour.

The pharmaceutical preparation may be present in a form suitable for oral, rectal, transdermal, ophthalmological, nasal, pulmonary or parenteral application. Preferably, the pharmaceutical preparation is suitable for oral administration; in that case it may be present in the form of tablets, coated tablets, capsules, granulate, solutions for drinking, liposomes, nano-particles, nano-capsules, micro-capsules, micro-tablets, pellets or powders as well as granulate filled in capsules, micro-tablets filled in capsules, pellets filled in capsules, nano-particles filled in capsules or powder filled in capsules. Preferably, the pharmaceutical preparation is present in the form of nano-particles, micro-pellets or micro-tablets which, optionally, may be filled in sachets or capsules. As a rule, these micro-pellets or micro-tablets have a diameter (without coating) of $\leq 5000$ μm, preferably 300 to 2000 μm.

Preferably, all solid oral dosage forms may be provided with an enteric coating. For example, this may be applied to the tablets, micro-tablets, micro-pellets etc., or coated onto the capsules containing them.

The forms of the pharmaceutical preparations of the invention may generally be prepared by the classic tabletting method, but also by direct compression, by the melt method in case of solid dispersions and by the spray drying method. If desired, an enteric coating may be applied in a conventional coating pan, sprayed on or applied in a fluid-bed apparatus. After drying is completed, a film coat may be applied in the same apparatus. If a mixture of active ingredients is used, it is possible to prepare pellets with the individual active ingredients and mixing them in the desired ratio, optionally after applying a film coat.

In case of parenteral application, the pharmaceutical preparation is present in a suitable form, for example as a sterile solution or emulsion. The correct formulations and suitable excipients are known to the skilled practitioner.

The pharmaceutical preparation of the invention contains an amount of oligomer suitable for the therapeutic purpose. This amount may be determined by the skilled practitioner by routine experimentation. As a rule, the pharmaceutical preparation will contain an amount of fumaric acid oligomer corresponding to 10 to 500 mg of fumaric acid, preferably 30 to 200 mg of fumaric acid, most preferably 100 mg of fumaric acid.

When compared with the known use of the monomers as active pharmaceutical preparation ingredients, the use of the oligomers of the invention has the advantage that, owing to their higher molecular weight, they are less volatile and therefore easier to handle during production and processing. The have the added benefit that, being synthetic substances, they have to be converted to endogenous substances in the body first, which increases their residence time in the organism. This conversion probably takes place by cleaving the substance into monomers. Owing to the oligomerisation, they also have the advantage of being less irritating on the mucous membrane and therefore have fewer side effects.

The invention will now be illustrated by the following examples which should not be construed as limiting.

EXAMPLES

Example 1

Preparation of Enteric-Coated Micro-Tablets in Capsules, Containing 60.0 mg of r-1,t-2,c-3,t-4-tetrakis (methoxycarbonyl)cyclobutane and 30.0 mg of r-1,t-2,c-3, t-4,c-5,t-6-hexa(methoxycarbonyl) cyclohexane 6.0 kg of r-1,t-2,c-3,t-4-tetrakis(methoxycarbonyl)cyclobutane and 3.0 kg of r-1,t-2, c-3,t-4,c-5,t-6-hexa(methoxycarbonyl)cyclohexane are crushed, mixed thoroughly and homogenised by means of a sieve 800. Then an excipient mixture with the following composition is prepared: 18.00 kg of starch derivative (STA-RX® 1500), 0.30 kg of microcrystalline cellulose (Avicel PH 101), 0.75 kg of PVP (Kollidon 120), 4.00 kg of Primogel, 0.25 kg of colloidal silicic acid (Aerosil). The active ingredient is added to the entire powder mixture, mixed, homogenised by means of a sieve 200, processed in the usual manner with a 2% aqueous solution of polyvinyl pyrrolidone (Kollidon K25) to obtain a binder granulate and then mixed in the dry state with the outer phase. Said outer phase consists of 0.50 kg of Mg stearate and 1.50 kg of talcum. Then the powder mixture is compressed in the usual manner to obtain convex tablets having a gross weight of 10.0 mg and a diameter of 2.0 mm.

In order to achieve resistance to gastric acid a solution of 2.250 kg of hydroxy propyl methyl cellulose phthalate (HP-MCCP, Pharmacoat® HP 50) is dissolved in portions in a mixture of the following solvents: 13.00 l of acetone, 13.50 l of dissolved ethanol (94 wt.-%, denatured with 2% of ketone) and 2.50 l of demineralised water. As a plasticiser, castor oil (0.240 kg) is added to the finished solution and applied in portions onto the tablet cores in the customary manner.

After drying is completed, a suspension of the following composition is applied as a film coat in the same apparatus: 0.340 kg of talcum, 0.400 kg of titanium(VI) oxide Cronus RN 56, 0.324 kg of coloured lacquer L-Rotlack 86837, 4.800 kg of Eudragit E 12.5% and 0.120 kg of polyethylene glycol 6000, pH 11 XI in a solvent mixture of the following composition: 8.170 kg of 2-propanol, 0.200 kg of demineralised water and 0.600 kg of glycerine triacetate (Triacetin).

After being analysed for their content of the active ingredient, the enteric-coated micro-tablets are filled into hard gelatine capsules at the appropriate net weight and sealed.

Example 2

Preparation of Enteric-Coated Micro-Tablets in Capsules, Containing 60.0 mg of r-1,t-2,c-3 t-4-tetrakis (methoxycarbonyl)cyclobutane and 30.0 mg of r-1,t-2,c-3,t-4,c-5 t-6-hexa(methoxycarbonyl)cyclohexane 6.0 kg of r-1,t-2,c-3,t-4-tetrakis(methoxycarbonyl)cyclobutane and 3.0 kg of r-1,t-2,c-3,t-4,c-5,t-6-hexa(methoxycarbonyl)cyclohexane are crushed, mixed thoroughly and homogenised by means of a sieve 800. Then an excipient mixture with the following composition is prepared: 24.70 kg of micro-crystalline cellulose (Avicel PH 200), 3.00 kg of croscarmellose sodium (AC-Di-SOL-SD-711), 2.50 kg of talcum, 0.10 kg of anhydrous silica (Aerosil 200) and 1.00 kg of magnesium stearate. The active ingredient is added to the entire powder mixture, mixed and homogenised. Then the powder mixture is compressed by the direct tabletting method to obtain convex micro-tablets having a gross weight of 10.0 mg and a diameter of 2.0 mm.

As an enteric coating, a solution of 0.94 kg of Eudragit L in isopropanol is prepared which also contains 0.07 kg of dibutyl phthalate. This solution is sprayed onto the tablet cores. After that, a dispersion of 17.32 kg of Eudragit L D-55 and a mixture of 2.80 kg of micro-talcum, 2.00 kg of Macrogol 6000 and 0.07 kg of dimeticon in water is prepared and sprayed onto the cores.

After being analysed for their content of the active ingredient, the enteric-coated micro-tablets are filled into hard gelatine capsules or sachets at the appropriate net weight and sealed.

Example 3

Preparation of Enteric-Coated Pellets in Capsules, Containing 60.0 mg of r-1,t-2,c-3,t-4-tetrakis(methoxycarbonyl)cyclobutane and 30.0 mg of r-1,t-2,c-3, t-4,c-5, t-6-hexa(methoxycarbonyl)cyclohexane 6.0 kg of r-1,t-2,c-3,t-4-tetrakis(methoxycarbonyl)cyclobutane and 3.0 kg of r-1,t-2,c-3,t-4,c-5,t-6-hexa(methoxycarbonyl)cyclohexane are crushed, mixed thoroughly and homogenised by means of a sieve 800. At the same tire, 2 l of a 20% (m/v) polyvinylpyrrolidone solution (Kollidon K30) in ethanol is prepared. 7.250 kg of nonpareilles pellets are coated in a coating pan and sprayed with one part of the Kollidon K-30 solution until slightly humid. After that, portions of the active ingredient mixture are added until the pellets are dry. This process of humidification/drying is continued until all of the active ingredient mixture has been added. The remainder of the PVP solution is mixed with 0.720 kg of Eudragit E 12.5% solution and all of it sprayed onto the pellets. The pellets are moved around until fully dry.

The pellets are sprayed with Eudragit S 12.5% solution and dried with talcum. After each spraying/drying cycle, the release of the active ingredients is measured and additional Eudragit S 12.5% solution/talcum added until a release meeting the specification is obtained.

After being analysed for their content of the active ingredient, the enteric-coated pellets are filled into capsules at the appropriate net weight.

Example 4

Preparation of Enteric-Coated Tablets Containing 120.0 mg of r-1,t-2,c-3,t-4-tetrakis(methoxycarbonyl)cyclobutane 12.0 kg of r-1,t-2,c-3,t-4-tetrakis(methoxycarbonyl)cyclobutane are crushed, mixed thoroughly and homogenised by means of a sieve 800. Then an excipient mixture with the following composition is prepared: 19.00 kg of starch derivative (STA-RX 1500®), 2.000 kg of micro-crystalline cellulose (Avicel PH 101®), 0.600 kg of polyvinyl pyrrolidone (PVP, Kollidon® 25), 4.000 kg of Primogel®, 0.300 kg of colloidal silicic acid (Aerosil®). The active ingredient is added to the entire powder mixture, mixed, homogenised by means of a sieve 200, and processed in the usual manner with a 2% aqueous solution of polyvidon pyrrolidone (PVP, Kollidon® 25) to obtain a binder granulate and then mixed in the dry state with the outer phase. Said outer phase consists of 2.000 kg of a so-called FST complex containing 80% of talcum, 10% of silicic acid and 10% Mg stearate. Then the powder mixture is compressed in the usual manner to obtain convex tablets having a gross weight of 400 mg and a diameter of 11.5 mm.

A solution of 2.250 kg of hydroxy propyl methyl cellulose phthalate (HPMCP, Pharmacoat HP® 50) is dissolved in a mixture of the following solvents: 2.50 l of demineralised water, 13.00 l of acetone Ph.Helv.VII and 13.00 l of ethanol, 94 wt.-% and 0.240 kg of castor oil (Ph.Eur.II) are added to the solution. In a coating pan, the solution is coated onto or sprayed on the tablet cores in the traditional manner.

After drying is completed, a film coat is applied which is composed of a solution of 4.800 kg of Eudragit E® 12.5%, 0.340 kg of talcum Ph.Eur. II, 0.520 kg of titanium(VI) oxide Cronus RN 56®, 0.210 kg of coloured lacquer ZLT-2 blue (Siegle), and 0.120 kg of polyethylene glycol 6000, Ph.Helv. VII in a solvent mixture of the following composition: 8.200 kg of 2-propanol Ph. Helv. VII, 0.060 kg of glycerine triacetate (Triacefin®) and 0.200 kg of demineralised water. After homogenous distribution in a fluidised bed, drying and polishing occurs as usual.

Example 5

Preparation of a Suspension for Parenteral Application, Containing 60.0 mg of r-1,t-2,c-3,t-4-tetrakis (methoxycarbonyl)cyclobutane and 30.0 mg of r-1,t-2, c-3,t-4,c-5,t-6-hexa(methoxycarbonyl) cyclohexane

| Ingredients | mg/ml |
| --- | --- |
| r-1, t-2, c-3, t-4-tetrakis(methoxycarbonyl)cyclobutane | 60.00 |
| r-1, t-2, c-3, t-4, c-5, t-6-hexa(methoxycarbonyl)cyclohexane | 30.00 |
| Methyl cellulose | 0.25 |
| Sodium citrate, dihydrate | 30.00 |
| Benzyl alcohol | 9.00 |
| Methylparaben | 1.80 |

-continued

| Ingredients | mg/ml |
| --- | --- |
| Propylparaben | 1.20 |
| Water for injection purposes q.s.a.d. | 1.00 |

Using standard techniques, the above-mentioned ingredients are processed into a parenteral suspension.

Example 6

Preparation of a Solution for Parenteral Application, Containing 30.0 mg of r-1,t-2,c-3,t-4-tetrakis(methoxycarbonyl)cyclobutane

| Ingredients | mg/ml |
| --- | --- |
| r-1, t-2, c-3, t-4-tetrakis(methoxycarbonyl)cyclobutane | 30.00 |
| Hydroxypropyl β-cyclodextrine | 300.00 |
| Sodium dihydrogen phosphate | 10.00 |
| Methylparaben | 0.75 |
| Monothioglycerol | 2.00 |
| Water for injection purposes q.s.a.d. | 1.00 |

Using standard techniques, the above-mentioned ingredients are processed into a parenteral solution.

The invention claimed is:

1. A pharmaceutical preparation comprising an oligomer of formula (I)

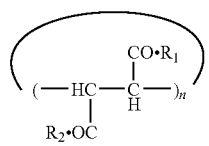

wherein
n is 2 or 3, $R_1$ is hydroxyl, $R_2$ is an alcohol radical (—$OR_5$), and $R_5$ is a $C_{1-24}$ alkyl radical, with the proviso that when n is 2, $R_5$ is not methyl; or n is 3, $R_1$ is hydroxyl, $R_2$ is an amine radical (—$NR_3R_4$) wherein $R_3$ and $R_4$ are the same or different and are independently chosen from hydrogen, $C_{1-24}$ alkyl radicals, a phenyl radical and $C_{6-10}$ aralkyl radicals; or n is 2 or 3, $R_1$ is an alcohol radical (—$OR_5$), $R_5$ is a $C_{1-24}$ alkyl radical, and $R_2$ is an amine radical (—$NR_3R_4$) wherein $R_3$ and $R_4$ are the same or different and are independently chosen from hydrogen, $C_{1-24}$ alkyl radicals, a phenyl radical and $C_{6-10}$ aralkyl radicals, or n is 2 or 3, $R_1$ and $R_2$ are independently chosen from alcohol radicals (—$OR_5$), wherein $R_5$ is a $C_{1-24}$ alkyl radical and wherein $R_1$ and $R_2$ are different and at least one excipient.

2. A pharmaceutical preparation according to claim 1 wherein the carbonyl groups carrying the radicals $R_1$ and $R_2$ are arranged as substituents in the trans position to each adjacent substituent.

3. A pharmaceutical preparation according to claim 1 wherein the oligomer of formula (I) is represented by formula (II)

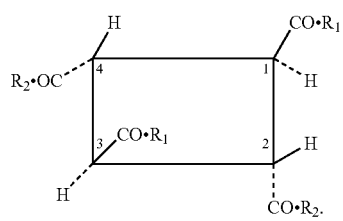

4. A pharmaceutical preparation according to claim 1 wherein the oligomer of formula (I) is represented by formula (III)

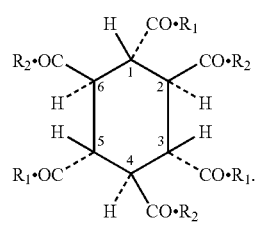

5. A pharmaceutical preparation according to claim 1, said pharmaceutical preparation being available in a form suitable for oral, rectal, transdermal, dermal, opthalmological, nasal, pulmonary or parenteral application.

6. A pharmaceutical preparation according to claim 1, said pharmaceutical preparation being present in the form of tablets, coated tablets, capsules, granulate, solutions for drinking, liposomes, nano-particles, nano-capsules, micro-capsules, micro-tablets, pellets, powders, granulate filled in capsules, micro-tablets filled in capsules, pellets filled in capsules, nano-particles filled in capsules or powder filled in capsules.

7. A pharmaceutical preparation according to claim 6, said pharmaceutical preparation being present in the form of nano-particles, micro-pellets or micro-tablets.

8. A pharmaceutical preparation according to claim 6 wherein the solid oral dosage forms further comprise an enteric coating.

9. A pharmaceutical preparation according to any of the claims 1 to 8 which contains an amount of an oligomer corresponding to 10 to 500 mg of fumaric acid.

10. A method for preparing a pharmaceutical preparation comprising admixing an oligomer of formula (I)

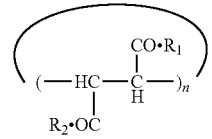

wherein
n is 2 or 3, $R_1$ is hydroxyl, $R_2$ is an alcohol radical (—$OR_5$), and $R_5$ is a $C_{1-24}$ alkyl radical, with the proviso that when n is 2, $R_5$ is not methyl; or n is 3, $R_1$ is hydroxyl, $R_2$ is an amine radical (—$NR_3R_4$) wherein $R_3$ and $R_4$ are the same or different and are independently chosen from hydrogen, $C_{1-24}$ alkyl radicals, a phenyl radical and $C_{6-10}$ aralkyl radicals; or n is 2 or 3, $R_1$ is an alcohol radical (—$OR_5$), $R_5$ is a $C_{1-24}$ alkyl radical, and $R_2$ is an amine radical (—$NR_3R_4$) wherein $R_3$ and $R_4$ are the same or different and are independently chosen from hydrogen, $C_{1-24}$ alkyl radicals, a phenyl radical and $C_{6-10}$ aralkyl radicals, or n is 2 or 3, $R_1$ and $R_2$ are independently chosen from alcohol radicals (—$OR_5$), wherein $R_5$ is a $C_{1-24}$ alkyl radical and wherein $R_1$ and $R_2$ are different with at least one excipient.

11. A pharmaceutical preparation according to claim 7, wherein said nano-particles, micro-pellets or micro-tablets are filled in sachets or capsules.

12. A method for preparing a pharmaceutical preparation according to claim 10 further comprising subjecting the admixture to tabletting, direct compression, melt methods, or spray drying to form tablets, granulates, nano-particles, nano-capsules, micro-capsules, micro-tablets, pellets, or powders.

13. A method for preparing a pharmaceutical preparation according to claim 12, wherein said tablets, granulates, nano-particles, nano-capsules, micro-capsules, micro-tablets, pellets, or powders are enterically coated.

14. A method for preparing a pharmaceutical preparation according to claim 12, wherein said nano-particles, nano-capsules, micro-capsules, micro-tablets, pellets, or powders are put into capsules.

15. A pharmaceutical preparation comprising an oligomer of formula (I)

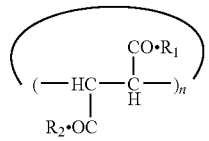

wherein n is 2 or 3, $R_1$ is hydroxyl, $R_2$ is an alcohol radical (—$OR_5$), and $R_5$ is a $C_{1-24}$ alkyl radical, with the proviso that when n is 2, $R_5$ is not methyl and at least one excipient.

16. A pharmaceutical preparation comprising an oligomer of formula (I)

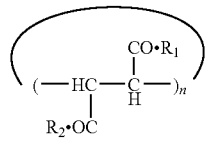

wherein n is 3, $R_1$ is hydroxyl, $R_2$ is an amine radical (—$NR_3R_4$), and $R_3$ and $R_4$ are the same or different and are independently chosen from hydrogen, $C_{1-24}$ alkyl radicals, a phenyl radical and $C_{6-10}$ aralkyl radicals, and at least one excipient.

17. A pharmaceutical preparation comprising an oligomer of formula (I)

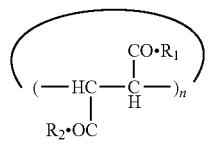

wherein n is 2 or 3, $R_1$ is an alcohol radical (—$OR_5$), $R_5$ is a $C_{1-24}$ alkyl radical, and $R_2$ is an amine radical (—$NR_3R_4$), wherein $R_3$ and $R_4$ are the same or different and are independently chosen from hydrogen, $C_{1-24}$ alkyl radicals, a phenyl radical and $C_{6-10}$ aralkyl radicals, and at least one excipient.

* * * * *